(12) United States Patent
Pretz et al.

(10) Patent No.: US 11,459,282 B2
(45) Date of Patent: *Oct. 4, 2022

(54) METHODS FOR FORMING LIGHT OLEFINS BY CRACKING

(71) Applicant: Dow Global Technologies LLC, Midland, MI (US)

(72) Inventors: Matthew T. Pretz, Freeport, TX (US); Yu Liu, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/491,331

(22) PCT Filed: Mar. 9, 2018

(86) PCT No.: PCT/US2018/021656
§ 371 (c)(1),
(2) Date: Sep. 5, 2019

(87) PCT Pub. No.: WO2018/169768
PCT Pub. Date: Sep. 20, 2018

(65) Prior Publication Data
US 2020/0017426 A1    Jan. 16, 2020

Related U.S. Application Data

(60) Provisional application No. 62/470,570, filed on Mar. 13, 2017.

(51) Int. Cl.
*C07C 4/06* (2006.01)
*C10G 11/18* (2006.01)
(Continued)

(52) U.S. Cl.
CPC .............. *C07C 4/06* (2013.01); *C07C 5/3337* (2013.01); *C07C 11/04* (2013.01); *C07C 11/06* (2013.01);
(Continued)

(58) Field of Classification Search
None
See application file for complete search history.

(56) References Cited

U.S. PATENT DOCUMENTS 4,051,013 A * 9/1977 Strother ................ B01J 8/26
208/78
4,579,716 A    4/1986 Krambeck et al.
(Continued)

FOREIGN PATENT DOCUMENTS

CA    2617580 C    2/2014
CA    2990639 A1    12/2016
(Continued)

OTHER PUBLICATIONS

Examination Report pertaining to G.C.C. Patent Application No. 2018-34837, dated Dec. 3, 2019.
(Continued)

*Primary Examiner* — Philip Y Louie
(74) *Attorney, Agent, or Firm* — Dinsmore & Shohl LLP (57) ABSTRACT

According to one or more embodiments presently disclosed, light olefins may be formed by a method that may comprise introducing a feed stream into a reactor, reacting the feed stream with a cracking catalyst in the reactor to form a product stream, and processing the cracking catalyst. The reactor may comprise an upstream reactor section and a downstream reactor section. The upstream reactor section may be positioned below the downstream reactor section. The upstream reactor section may have an average cross-
(Continued)

sectional area that is at least 150% of the average cross-sectional area of the downstream reactor section.

16 Claims, 3 Drawing Sheets

(51) Int. Cl.
  *C07C 5/333* (2006.01)
  *C07C 11/04* (2006.01)
  *C07C 11/06* (2006.01)
  *C07C 11/08* (2006.01)
(52) U.S. Cl.
  CPC ............ *C07C 11/08* (2013.01); *C10G 11/182* (2013.01); *C07C 2523/42* (2013.01); *C07C 2529/068* (2013.01); *C10G 2300/1044* (2013.01); *C10G 2400/20* (2013.01)

(56) References Cited

U.S. PATENT DOCUMENTS

| | | | |
|---|---|---|---|
| 4,595,567 A * | 6/1986 | Hedrick | B01J 8/125 122/4 D |
| 5,190,650 A | 3/1993 | Tammera et al. | |
| 5,275,641 A | 1/1994 | Tammera et al. | |
| 5,456,821 A * | 10/1995 | Absil | B01J 27/16 208/114 |
| 7,128,827 B2 | 10/2006 | Tallman et al. | |
| 7,396,971 B2 | 8/2008 | Smith et al. | |
| 7,491,315 B2 | 2/2009 | Eng et al. | |
| 7,575,725 B2 | 8/2009 | Lomas et al. | |
| 7,585,489 B2 | 9/2009 | Abrevaya et al. | |
| 8,157,985 B2 | 4/2012 | Nicholas et al. | |
| 8,669,406 B2 | 3/2014 | Pretz et al. | |
| 9,284,235 B2 | 3/2016 | Liu et al. | |
| 9,370,759 B2 | 6/2016 | Pretz et al. | |
| 9,725,382 B2 | 8/2017 | Pretz et al. | |
| 2002/0024276 A1 | 2/2002 | Neuhaus | |
| 2004/0024276 A1 | 2/2004 | Smith et al. | |
| 2004/0104148 A1 | 6/2004 | Lomas et al. | |
| 2010/0016648 A1 | 1/2010 | Qi et al. | |
| 2011/0112345 A1 | 5/2011 | Chewter et al. | |
| 2011/0251046 A1 | 10/2011 | Niccum et al. | |
| 2011/0275874 A1 | 11/2011 | Li et al. | |
| 2014/0115952 A1 | 5/2014 | Wang et al. | |
| 2014/0275675 A1 * | 9/2014 | Eng | C10G 3/46 585/303 |
| 2016/0272559 A1 | 9/2016 | Pretz et al. | |
| 2016/0362613 A1 | 12/2016 | Cunningham et al. | |
| 2020/0017427 A1 * | 1/2020 | Pretz | C07C 1/24 |

FOREIGN PATENT DOCUMENTS

| | | |
|---|---|---|
| CN | 203448073 U | 2/2014 |
| CN | 104437274 A | 3/2015 |
| EP | 127116 B1 | 7/1988 |
| EP | 2172440 A1 | 4/2010 |
| EP | 1555308 B1 | 10/2010 |
| IN | 253588 | 8/2012 |
| IN | 201404173 P1 | 4/2016 |
| WO | 2015073152 A1 | 5/2015 |
| WO | 2017058854 A1 | 4/2017 |

OTHER PUBLICATIONS

International Search Report and Written Opinion pertaining to PCT/US2018/021658, dated Jun. 6, 2018.
International Search Report and Written Opinion pertaining to PCT/US2018/021656, dated May 14, 2018.
Zamostny et al, "A Multipurpose Micro-pulse Reactor for Studying Gas-phase Reactions", Chemical and Biochemical Engineering Quarterly, 2007, 107-108.
Examination Report pertaining to corresponding G.C.C. Patent Application No. GC 2018-34837, dated Aug. 26, 2019.
Office Action dated Jun. 25, 2020 pertaining to U.S. Appl. No. 16/491,318, filed Sep. 5, 2019, 30 pgs.
Andersen "Technologies for Filling the Propylene Gap" 2005 UOP pp. 1-19 (Year: 2005).
Examination Report pertaining to G.C.C. Patent Application No. 2018-34838, dated Oct. 6, 2020.
Office Action dated May 28, 2021 pertaining to U.S. Appl. No. 16/491,318, filed Sep. 5, 2019, 16 pgs.
Chinese Office Action dated Nov. 11, 2021 pertaining to Chinese Application No. 201880012341.7 filed Mar. 9, 2018, 7 pages.
Chinese Search Report dated Nov. 11, 2021 pertaining to Chinese Application No. 201880012341.7 filed filed Mar. 9, 2018, 2 pages.
U.S. Office Action dated Jan. 27, 2022 pertaining to U.S. Appl. No. 16/491,318, filed Sep. 5, 2019, 19 pages.
Article 94(3) dated May 4, 2022, pertaining to EP Patent Application No. 18712415.1, 6 pgs.

* cited by examiner

METHODS FOR FORMING LIGHT OLEFINS BY CRACKING

CROSS-REFERENCE TO RELATED APPLICATIONS

This application claims priority to U.S. Provisional Patent Application No. 62/470,570, filed Mar. 13, 2017, entitled "Methods And Apparatuses For Forming Light Olefins By Cracking", the contents of which are hereby incorporated by reference in their entirety.

BACKGROUND

Field

The present disclosure generally relates to chemical processing, and more specifically, to reactor designs and systems utilized in cracking reactions to from light olefins.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene. However, most light olefins must be produced by different reaction processes based on the given chemical feed stream, which may be a product stream from a crude oil refining operation.

BRIEF SUMMARY

There is a continued need for processes and apparatuses which are suitable for producing light olefins by cracking. Disclosed herein are apparatuses and methods for cracking hydrocarbon streams, such as naphtha or butane, to form light olefins. The process configurations presently disclosed, such as utilizing a reactor which comprises an upstream reactor section positioned below a downstream reactor section, where the upstream reactor section has an average cross-sectional area that is at least 150% of the average cross-sectional area of the downstream reactor section, are suitable for cracking of naphtha or butane to form light olefins. Such a reactor design may operate as a fast fluidized, turbulent, or bubbling bed upflow reactor in its upstream reactor section, and as a dilute phase riser reactor in its downstream reactor section.

Additionally, of advantage in some embodiments of the presently disclosed methods and reactor systems is the processing flexibility offered by the presently disclosed reactor design. In some embodiments, the reactor design disclosed herein may be utilized for additional processes, other than cracking, that can be utilized to make olefins from other feedstocks. For example, light olefins may be produced from a variety of feed stream by utilizing different catalysts. For example, light olefins may be produced by at least dehydrogenation reactions, cracking reactions, dehydration reactions, and methanol-to-olefin reactions. However, according to various embodiments, these reaction types may utilize different feed streams to form the light olefins. Non-limiting examples include utilizing a dehydrogenation reaction that may utilize a gallium and/or platinum catalyst to react a feed stream comprising one or more of ethane, propane, n-butane, and i-butane; a cracking reaction that may utilize a zeolite catalyst to react a feed stream comprising one or more of naphtha, n-butane, or i-butane; a dehydration reaction that may utilize an acid catalyst (such as alumina or zeolite) to react a feed stream comprising one or more of ethanol, propanol, or butanol; and a methanol-to-olefin reaction that may utilize a zeolite (such as SAPO-34) catalyst to react a feed stream comprising methanol.

In some embodiments, the presently disclosed reactors, which may be utilized for cracking reactions, may be suitable for other types of reactions. For example, the presently described reactor system may be also operable, in addition to cracking, to perform dehydrogenation, dehydration, and/or methanol-to-olefin reactions. This feature may allow for the selection of feedstocks based on their price and availability, decreasing costs in producing light olefins. As such, it should be understood that in some embodiments, the reactors and processes may purposefully not be fully optimized for cracking reactions, with the intent for allowing flexibility of the disclosed reactors for other reaction processes to form olefins.

Additionally, according to various embodiments, the reactor systems and methods described herein may utilize a supplemental fuel to heat the catalyst in a catalyst processing step. The supplemental fuel may be suitable for heating the catalysts of the presently described reactions because, unlike in many reactions which may form olefins, coke or other combustible materials may not be produced in sufficient quantity in the presently disclosed reactions. For example, the cracking of naphtha or butane may not form sufficient coke on the catalyst to burn to generate heat. Therefore, since heat is needed for the cracking reaction and it cannot be supplied by burning coke, a supplemental fuel source may be utilized, such as a liquid or vapor supplemental fuel source.

According to one embodiment, olefins may be formed by a method that may comprise introducing a feed stream into a reactor, reacting the feed stream with a cracking catalyst in the reactor to form a product stream, and processing the cracking catalyst. The reactor may comprise an upstream reactor section and a downstream reactor section. The upstream reactor section may be positioned below the downstream reactor section. The upstream reactor section may have an average cross-sectional area that is at least 150% of the average cross-sectional area of the downstream reactor section. The processing of the cracking catalyst may comprise passing the catalyst from the reactor to a combustor, burning a supplemental fuel source in the combustor to heat the catalyst, and passing the heated catalyst from the combustor to the reactor.

According to another embodiment, olefins may be formed by a method that may comprise introducing a feed stream into a reactor, reacting the feed stream with a cracking catalyst in the reactor to form a product stream, and processing the cracking catalyst. The reactor may comprise an upstream reactor section and a downstream reactor section. The upstream reactor section may operate as a fast fluidized or turbulent upflow reactor, and the downstream reactor section may operate as a plug flow reactor. The upstream reactor section may be positioned below the downstream reactor section. The upstream reactor section may have an average cross-sectional area that is at least 150% of the average cross-sectional area of the downstream reactor section. The processing of the cracking catalyst may comprise passing the catalyst from the reactor to a combustor, burning a supplemental fuel source in the combustor to heat the catalyst, and passing the heated catalyst from the combustor to the reactor.

According to another embodiment, olefins may be formed by a method that may comprise introducing a feed stream into a reactor, reacting the feed stream with a cracking catalyst in the reactor to form a product stream, and processing the cracking catalyst. The feed stream may comprise one or more of naphtha or butane, and the product stream may comprise one or more of ethylene, propylene, or butene. The reactor may comprise an upstream reactor section and a downstream reactor section. The upstream reactor section may be positioned below the downstream reactor section. The upstream reactor section may have an average cross-sectional area that is at least 150% of the average cross-sectional area of the downstream reactor section. The processing of the cracking catalyst may comprise passing the catalyst from the reactor to a combustor, burning a supplemental fuel source in the combustor to heat the catalyst, and passing the heated catalyst from the combustor to the reactor.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments related to methods for processing chemical streams are disclosed herein. In one or more embodiments, the chemical stream that is processed may be referred to as a feed stream, which is processed by a reaction to form a product stream. In one or more embodiments, the feed stream may comprise one or more of naphtha or butane. Butane is defined as either n-butane or iso-butane or a combination of both. The feed stream may be converted by reaction to a product stream which may comprise one or more of ethylene, propylene, or butene. Ethylene, propylene, and butene may be referred to herein as "light olefins." As described herein, butene many include any isomer of butene, such as α-butylene, cis-β-butylene, trans-β-butylene, and isobutylene.

In one embodiment, the product stream may comprise at least 50 wt. % light olefins. For example, the product stream may comprise at least 60 wt. % light olefins, at least 70 wt. % light olefins, at least 80 wt. % light olefins, at least 90 wt. % light olefins, at least 95 wt. % light olefins, or even at least 99 wt. % light olefins.

In another embodiment, the feed stream may comprise at least 50 wt. % of naphtha. For example, the feed stream may comprise at least 60 wt. % naphtha, at least 70 wt. % naphtha, at least 80 wt. % naphtha, at least 90 wt. % naphtha, at least 95 wt. % naphtha, or even at least 99 wt. % naphtha. In another embodiment, the feed stream may comprise at least 50 wt. % butane. For example, the feed stream may comprise at least 60 wt. % butane, at least 70 wt. % butane, at least 80 wt. % butane, at least 90 wt. % butane, at least 95 wt. % butane, or even at least 99 wt. % butane. In yet another embodiment, the feed stream may comprise one or both of naphtha and butane, and the sum of naphtha and butane in the feed stream may be at least 50 wt. %. For example, the sum of naphtha and butane in the feed stream may be at least 60 wt. %, 70 wt. %, 80 wt. %, 90 wt. %, 95 wt. % or even 99 wt. %.

According to one or more embodiments, the reaction which converts the contents of the feed stream to the contents of the product stream may be a cracking reaction. A cracking reaction may break carbon-carbon bonds in a hydrocarbon. For example, in various cracking reactions, alkanes may be converted to shorter alkanes and alkenes. The cracking reaction may utilize a cracking catalyst. A cracking catalyst may be any catalyst capable of cracking one or more components of the feed stream. According to one embodiment, the cracking catalyst comprises one or more zeolites, such as ZSM-5 zeolite. In additional embodiments, the cracking catalyst may comprise, in addition to a catalytically active material, platinum. For example, the cracking catalyst may include from 0.001 wt. % to 0.05 wt. % of platinum. The platinum may be sprayed on as platinum nitrate and calcined at an elevated temperature, such as around 700° C. Without being bound by theory, it is believed that the addition of platinum to the catalyst may allow for easier combustion of supplemental fuels, such as methane.

Figure 1:
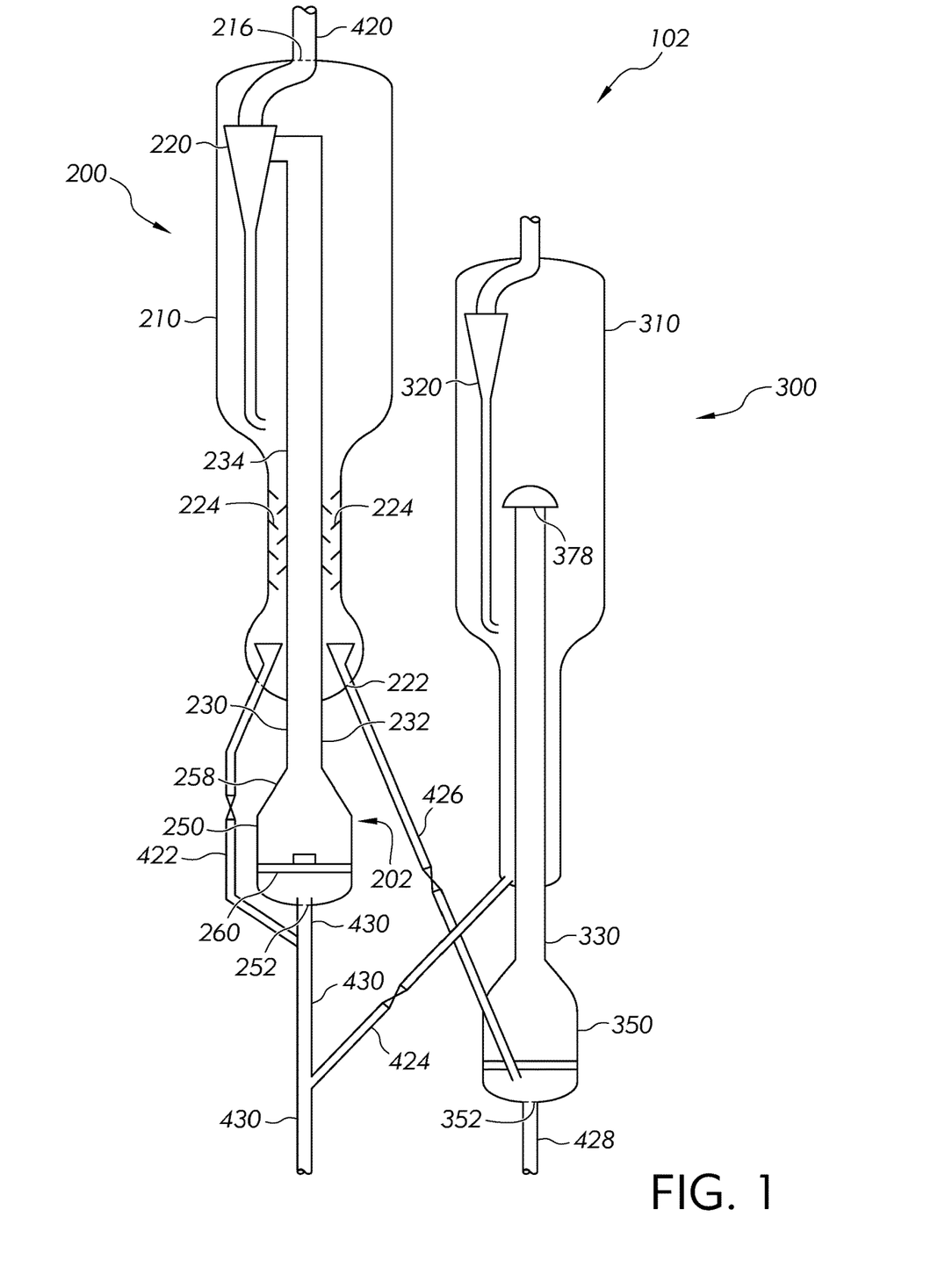
FIG. 1 schematically depicts a reactor system, according to one or more embodiments described herein.

Now referring to FIG. 1, an example reactor system 102 which may be suitable for use with the methods described herein is schematically depicted. However, it should be understood that other reactor system configurations may be suitable for the methods described herein. The reactor system 102 generally comprises multiple system components, such as a reactor portion 200 and/or a catalyst processing portion 300. As used herein in the context of FIG. 1, the reactor portion 200 generally refers to the portion of a reactor system 102 in which the major process reaction takes place, such as the cracking of naphtha or butane to form light olefins. The reactor portion 200 comprises a reactor 202 which may include a downstream reactor section 230 and an upstream reactor section 250. According to one or more embodiments, as depicted in FIG. 1, the reactor portion 200 may additionally include a catalyst separation section 210 which serves to separate the catalyst from the chemical products formed in the reactor 202. Also, as used herein, the catalyst processing portion 300 generally refers to the portion of a reactor system 102 where the catalyst is in some way processed, such as by combustion. The catalyst processing portion 300 may comprise a combustor 350 and a riser 330, and may optionally comprise a catalyst separation section 310. In some embodiments, the catalyst may be regenerated by burning off contaminants like coke in the catalyst processing portion 300. In additional embodiments, the catalyst may be heated in the catalyst processing portion 300. A supplemental fuel may be utilized to heat the catalyst in the catalyst processing portion 300 if coke or another combustible material is not formed on the catalyst, or an amount of coke formed on the catalyst is not sufficient to burn off to heat the catalyst to a desired temperature (which may be the case when cracking naphtha or butane). In one or more embodiments, the catalyst separation section 210 may be in fluid communication with the combustor 350 (e.g., via standpipe 426) and the catalyst separation section 310 may be in fluid communication with the upstream reactor section 250 (e.g., via standpipe 424 and transport riser 430).

As described with respect to FIG. 1, the feed stream may enter transport riser 430, and the product stream may exit the reactor system 102 via pipe 420. According to one or more embodiments, the reactor system 102 may be operated by feeding a chemical feed (e.g., in a feed stream) and a fluidized catalyst into the upstream reactor section 250. The chemical feed contacts the catalyst in the upstream reactor section 250, and each flow upwardly into and through the downstream reactor section 230 to produce a chemical product. The chemical product and the catalyst may be passed out of the downstream reactor section 230 to a separation device 220 in the catalyst separation section 210, where the catalyst is separated from the chemical product, which is transported out of the catalyst separation section 210. The separated catalyst is passed from the catalyst separation section 210 to the combustor 350. In the combustor 350, the catalyst may be processed by, for example, combustion. For example, and without limitation, the catalyst may be de-coked and/or supplemental fuel may be combusted to heat the catalyst. The catalyst is then passed out of the combustor 350 and through the riser 330 to a riser termination separator 378, where the gas and solid components from the riser 330 are at least partially separated. The vapor and remaining solids are transported to a secondary separation device 320 in the catalyst separation section 310 where the remaining catalyst is separated from the gases from the catalyst processing (e.g., gases emitted by combustion of spent catalyst or supplemental fuel). The separated catalyst is then passed from the catalyst separation section 310 to the upstream reactor section 250 via standpipe 424 and transport riser 430, where it is further utilized in a catalytic reaction. Thus, the catalyst, in operation, may cycle between the reactor portion 200 and the catalyst processing portion 300. In general, the processed chemical streams, including the feed streams and product streams may be gaseous, and the catalyst may be fluidized particulate solid.

According to one or more embodiments described herein, the reactor portion 200 may comprise an upstream reactor section 250, a transition section 258, and a downstream reactor section 230, such as a riser. The transition section 258 may connect the upstream reactor section 250 with the downstream reactor section 230. According to one or more embodiments, the upstream reactor section 250 and the downstream reactor section 230 may each have a substantially constant cross-section area, while the transition section 258 may be tapered and does not have a constant cross-sectional area. As described herein, unless otherwise explicitly stated, the "cross-sectional area" refers to the area of the cross section of a portion of the reactor part in a plane substantially orthogonal to the direction of general flow of reactants and/or products. For example, in FIG. 1, the cross sectional area of the upstream reactor section 250, the transition section 258, and the downstream reactor section 230 is in the direction of a plane defined by the horizontal direction and the direction into the page (orthogonal to the direction of fluid motion, i.e., vertically upward in FIG. 1).

As depicted in FIG. 1, the upstream reactor section 250 may be positioned below the downstream reactor section 230. Such a configuration may be referred to as an upflow configuration in the reactor 202.

As described herein, the upstream reactor section 250 may include a vessel, drum, barrel, vat, or other container suitable for a given chemical reaction. In one or more embodiments, the upstream reactor section 250 may be generally cylindrical in shape (i.e., having a substantially circular cross-sectional shape), or may alternately be non-cylindrically shaped, such as prism shaped with cross-sectional shapes of triangles, rectangles, pentagons, hexagons, octagons, ovals, or other polygons or curved closed shapes, or combinations thereof. The upstream reactor section 250, as used throughout this disclosure, may generally include a metallic frame, and may additionally include refractory linings or other materials utilized to protect the metallic frame and/or control process conditions. As depicted in FIG. 1, the upstream reactor section 250 may include a lower reactor portion catalyst inlet port 252 defining the connection of transport riser 430 to the upstream reactor section 250.

The upstream reactor section 250 may be connected to a transport riser 430 which, in operation, may provide processed catalyst and/or reactant chemicals in a feed stream to the reactor portion 200. The processed catalyst and/or reactant chemicals may be mixed with a distributor 260 housed in the upstream reactor section 250. The catalyst entering the upstream reactor section 250 via transport riser 430 may be passed through standpipe 424 to a transport riser 430, thus arriving from the catalyst processing portion 300. In some embodiments, catalyst may come directly from the catalyst separation section 210 via standpipe 422 and into a transport riser 430, where it enters the upstream reactor section 250. The catalyst can also be fed via 422 directly to the upstream reactor section 250. This catalyst may be slightly deactivated, but may still, in some embodiments, be suitable for reaction in the upstream reactor section 250. As used herein, "deactivated" may refer to a catalyst which is contaminated with a substance such as coke, or is cooler in temperature than desired. Regeneration may remove the contaminant such as coke, raise the temperature of the catalyst, or both.

Still referring to FIG. 1, the reactor portion 200 may comprise a downstream reactor section 230 which acts to transport reactants, products, and/or catalyst from the upstream reactor section 250 to the catalyst separation section 210. In one or more embodiments, the downstream reactor section 230 may be generally cylindrical in shape (i.e., having a substantially circular cross-sectional shape), or may alternately be non-cylindrically shaped, such as prism shaped with cross-sectional shape of triangles, rectangles, pentagons, hexagons, octagons, ovals, or other polygons or curved closed shapes, or combinations thereof. The downstream reactor section 230, as used throughout this disclosure, may generally include a metallic frame, and may additionally include refractory linings or other materials utilized to protect the metallic frame and/or control process conditions.

According to some embodiments, the downstream reactor section 230 may include an external riser section 232 and an internal riser section 234. As used herein, an "external riser section" refers to the portion of the riser that is outside of the catalyst separation section, and an "internal riser section" refers to the portion of the riser that is within the catalyst separation section. For example, in the embodiment depicted in FIG. 1, the internal riser section 234 of the reactor portion 200 may be positioned within the catalyst separation section 210, while the external riser section 232 is positioned outside of the catalyst separation section 210.

As depicted in FIG. 1, the upstream reactor section 250 may be connected to the downstream reactor section 230 via the transition section 258. The upstream reactor section 250 may generally comprise a greater cross-sectional area than the downstream reactor section 230. The transition section 258 may be tapered from the size of the cross-section of the upstream reactor section 250 to the size of the cross-section of the downstream reactor section 230 such that the transition section 258 projects inwardly from the upstream reactor section 250 to the downstream reactor section 230.

In some embodiments, such as those where the upstream reactor section 250 and the downstream reactor section 230 have similar cross-sectional shapes, the transition section 258 may be shaped as a frustum. For example, for an embodiment of a reactor portion 200 comprising a cylindrical upstream reactor section 250 and cylindrical downstream reactor section 230, the transition section 258 may be shaped as a conical frustum. However, it should be understood that a wide variety of upstream reactor section 250 shapes are contemplated herein which connect various shapes and sizes of upstream reactor section 250 and downstream reactor section 230.

In one or more embodiments, the upstream reactor section 250 may have an average cross-sectional area that is at least 150% of the average cross-sectional area of the downstream reactor section 230. As described herein, an "average cross-sectional area" refers to the mean of the cross-sectional areas for a given system component or section such as the upstream reactor section 250 or the downstream reactor section 230. If the system component or section has a substantially constant cross-sectional area, such as the cylindrical shapes of the depicted upstream reactor section 250 or the downstream reactor section 230, then the cross-sectional area at any point is about equal to the average cross-sectional area.

According to one or more embodiments, the upstream reactor section 250 may have an average cross-sectional area that is at least 160%, at least 170%, at least 180%, at least 190%, at least 200%, at least 250%, at least 300%, at least 400% or even at least 500% of the average cross-sectional area of the downstream reactor section 230.

In one or more embodiments, based on the shape, size, and other processing conditions such as temperature and pressure in the upstream reactor section 250 and the downstream reactor section 230, the upstream reactor section 250 may operate in a manner that is or approaches isothermal, such as in a fast fluidized, turbulent, or bubbling bed upflow reactor, while the downstream reactor section 230 may operate in more of a plug flow manner, such as in a riser reactor. For example, the reactor 202 of FIG. 1 may comprise an upstream reactor section 250 operating as a fast fluidized, turbulent, or bubbling bed reactor and a downstream reactor section 230 operating as a dilute phase riser reactor, with the result that the average catalyst and gas flow moves concurrently upward. As the term is used herein, "average flow" refers to the net flow, i.e., the total upward flow minus the retrograde or reverse flow, as is typical of the behavior of fluidized particles in general. As described herein, a "fast fluidized" reactor may refer to a reactor utilizing a fluidization regime wherein the superficial velocity of the gas phase is greater than the choking velocity and may be semi-dense in operation. As described herein, a "turbulent" reactor may refer to a fluidization regime where the superficial velocity of less than the choking velocity and is more dense than the fast fluidized regime. As described herein, a "bubbling bed" reactor may refer to a fluidization regime wherein well defined bubbles in a highly dense bed are present in two distinct phases. The "choking velocity" refers to the minimum velocity required to maintain solids in the dilute-phase mode in a vertical conveying line. As described herein, a "dilute phase riser" may refer to a riser reactor operating at transport velocity, where the gas and catalyst have about the same velocity in a dilute phase.

In one or more embodiments, the pressure in the reactor 202 may range from 6.0 to 44.7 pounds per square inch absolute (psia, from about 41.4 kilopascals, kPa, to about 308.2 kPa), but in some embodiments, a narrower selected range, such as from 15.0 psia to 35.0 psia, (from about 103.4 kPa to about 241.3 kPa), may be employed. For example, the pressure may be from 15.0 psia to 30.0 psia (from about 103.4 kPa to about 206.8 kPa), from 17.0 psia to 28.0 psia (from about 117.2 kPa to about 193.1 kPa), or from 19.0 psia to 25.0 psia (from about 131.0 kPa to about 172.4 kPa). Unit conversions from standard (non-SI) to metric (SI) expressions herein include "about" to indicate rounding that may be present in the metric (SI) expressions as a result of conversions.

In additional embodiments, the weight hourly space velocity (WHSV) for the disclosed process may range from 0.1 pound (lb) to 100 lb of chemical feed per hour (h) per lb of catalyst in the reactor (lb feed/h/lb catalyst). For example, where a reactor comprises an upstream reactor section 250 that operates as a fast fluidized, turbulent, or bubbling bed reactor and a downstream reactor section 230 that operates as a dilute phase riser reactor, the superficial gas velocity may range therein from 2 ft/s (about 0.61 m/s) to 10 ft/s (about 3.05 m/s) in the upstream reactor section 250, and from 30 ft/s (about 9.14 m/s) to 70 ft/s (about 21.31 m/s) in the downstream reactor section 230. In additional embodiments, a reactor configuration that is fully of a riser type may operate at a single high superficial gas velocity, for example, in some embodiments at least 30 ft/s (about 9.15 m/s) throughout.

In additional embodiments, the ratio of catalyst to feed stream in the reactor 202 may range from 5 to 100 on a weight to weight (w/w) basis. In some embodiments, the ratio may range from 10 to 40, such as from 12 to 36, or from 12 to 24.

In additional embodiments, the catalyst flux may be from 1 pound per square foot-second (lb/ft$^2$-s) (about 4.89 kg/m²–s) to 20 lb/ft²–s (to about 97.7 kg/m2–s) in the upstream reactor section 250, and from 10 lb/ft²–s (about 48.9 kg/m2–s) to 100 lb/ft²–s (about 489 kg/m2–s) in the downstream reactor section 230.

In operation, the catalyst may move upward through the downstream reactor section 230 (from the upstream reactor section 250), and into the separation device 220. The separated vapors may be removed from the reactor system 102 via a pipe 420 at a gas outlet port 216 of the catalyst separation section 210. According to one or more embodiments, the separation device 220 may be a cyclonic separation system, which may include two or more stages of cyclonic separation. In embodiments where the separation device 220 comprises more than one cyclonic separation stages, the first separation device into which the fluidized stream enters is referred to a primary cyclonic separation device. The fluidized effluent from the primary cyclonic separation device may enter into a secondary cyclonic separation device for further separation. Primary cyclonic separation devices may include, for example, primary cyclones, and systems commercially available under the names VSS (commercially available from UOP), LD2 (commercially available from Stone and Webster), and RS2 (commercially available from Stone and Webster). Primary cyclones are described, for example, in U.S. Pat. Nos. 4,579,716; 5,190,650; and 5,275,641, which are each incorporated by reference in their entirety herein. In some separation systems utilizing primary cyclones as the primary cyclonic separation device, one or more set of additional cyclones, e.g. secondary cyclones and tertiary cyclones, are employed for further separation of the catalyst from the product gas. It should be understood that any primary cyclonic separation device may be used in embodiments of the invention.

According to one or more embodiments, following separation from vapors in the separation device 220, the catalyst may generally move through the stripper 224 to the catalyst outlet port 222 where the catalyst is transferred out of the reactor portion 200 via standpipe 426 and into the catalyst processing portion 300. Optionally, the catalyst may also be transferred directly back into the upstream reactor section 250 via standpipe 422. Alternatively, the catalyst may be premixed with processed catalyst in the transport riser 430.

As is described in detail in accordance with the embodiment of FIG. 1, according to one or more embodiments, the catalyst may be processed by one or more of the steps of passing the catalyst from the reactor 202 to the combustor 350, burning a supplemental fuel source in the combustor 350 to heat the catalyst, and passing the heated catalyst from the combustor 350 to the reactor 202.

Referring now to the catalyst processing portion 300, as depicted in FIG. 1, the combustor 350 of the catalyst processing portion 300 may include one or more lower reactor portion inlet ports 352 and may be in fluid communication with the riser 330. The combustor 350 may be in fluid communication with the catalyst separation section 210 via standpipe 426, which may supply spent catalyst from the reactor portion 200 to the catalyst processing portion 300 for regeneration. The combustor 350 may include an additional lower reactor section inlet port 352 where air inlet 428 connects to the combustor 350. The air inlet 428 may supply reactive gases which may react with the spent catalyst or a supplemental fuel to at least partially regenerate the catalyst. For example, the catalyst may be coked following the reactions in the upstream reactor section 250, and the coke may be removed from the catalyst (i.e., regenerating the catalyst) by a combustion reaction. For example, oxidizer (such as air) may be fed into the combustor 350 via the air inlet 428. Alternatively or additionally, such as when coke is not formed on the catalyst, a supplemental fuel may be injected into the combustor 350, which may be burned to heat the catalyst. Following combustion, the processed catalyst may be separated in the catalyst separation section 310 and delivered back into the reactor portion 200 via standpipe 424.

In one embodiment, a vapor supplemental fuel may be added to the combustor 350 and burned to heat the catalyst. For example, suitable vapor fuels may include methane, natural gas, ethane, propane, hydrogen or any gas that comprises energy value upon combustion. According to another embodiment, a liquid supplemental fuel may be added to the combustor 350 and burned to heat the catalyst. Suitable liquid supplemental fuels include, without limitation, fuel oil, kerosene, naphtha, heavy cracking products, or other liquids with suitable fuel value for combustion.

Figure 2:
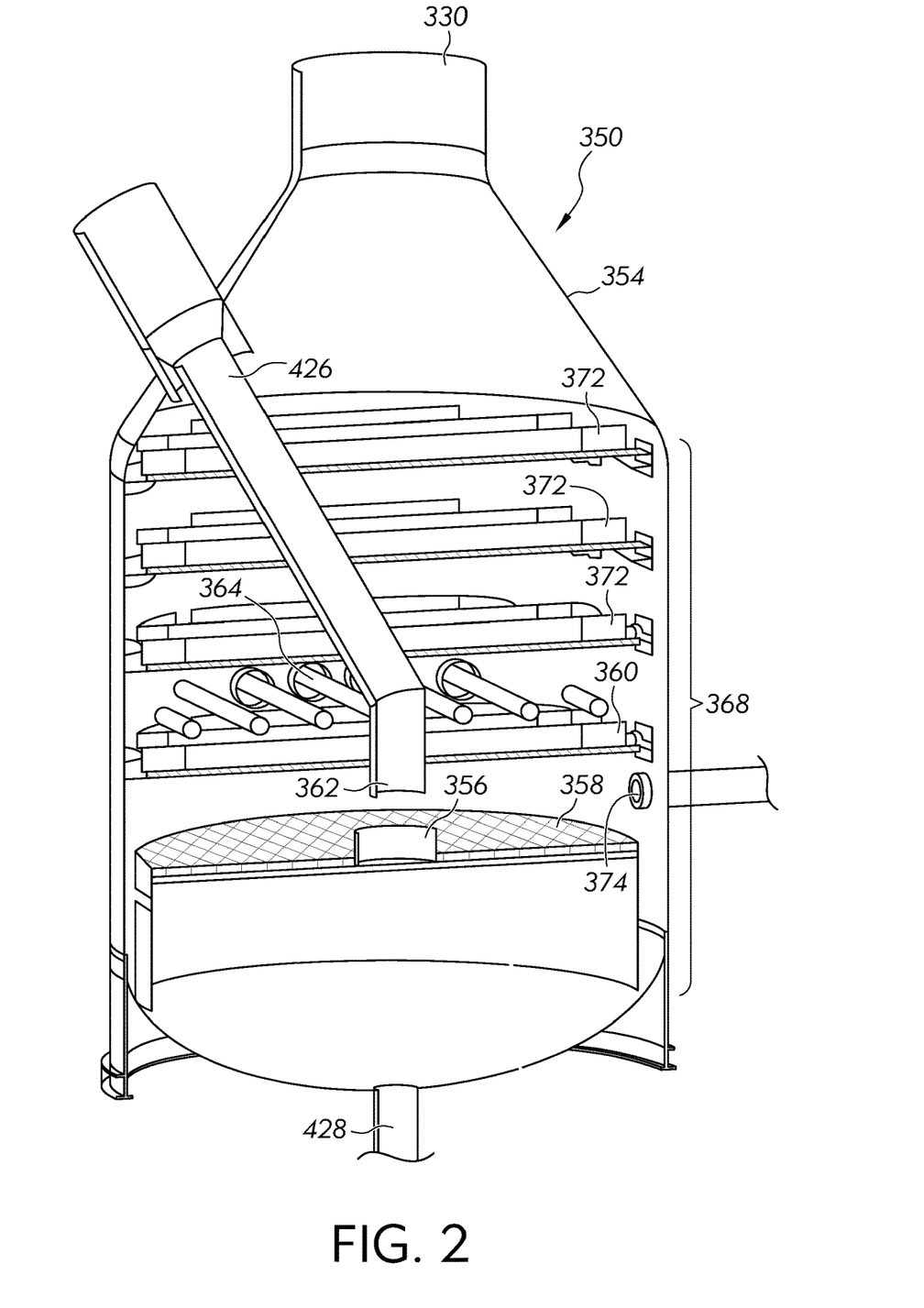
FIG. 2 schematically depicts a cutaway elevational view of a combustor, according to one or more embodiments described herein.

Referring NOW to FIG. 2, a cutaway elevational view of an embodiment of a combustor 350 suitable for use with the reactor system of FIG. 1 is depicted. Combustor 350 may include a lower portion 368 generally in the shape of a cylinder and an upper frustum section 354. Spent or partially deactivated catalyst may enter the combustor 350 through standpipe 426. The used catalyst may impinge upon and be distributed by splash guard 356. The combustor 350 may further include air distributors 358 which are located at or slightly below the height of the splash guard 356. Above the air distributors 358 and the outlet 362 of standpipe 426 is a grid 360. Above the grid 360 are a plurality of fuel gas distributors 364. One or more additional grids 372 may be positioned within the vessel above the fuel gas distributors 364. Further details of embodiments which include injection means for vapor supplemental fuel are available in U.S. application Ser. No. 14/868,507, filed Sep. 29, 2015, which is incorporated by reference herein in its entirety.

In additional embodiments, the combustor 350 may include one or more liquid injection port(s) 374. The liquid injection port may be utilized to inject liquid, combustible supplemental fuels into the combustor 350. While FIG. 2 depicts one liquid injection port 374, it is contemplated that, in additional embodiments, two or more liquid injection ports 374 may be incorporated into the combustor 350.

Figure 3:
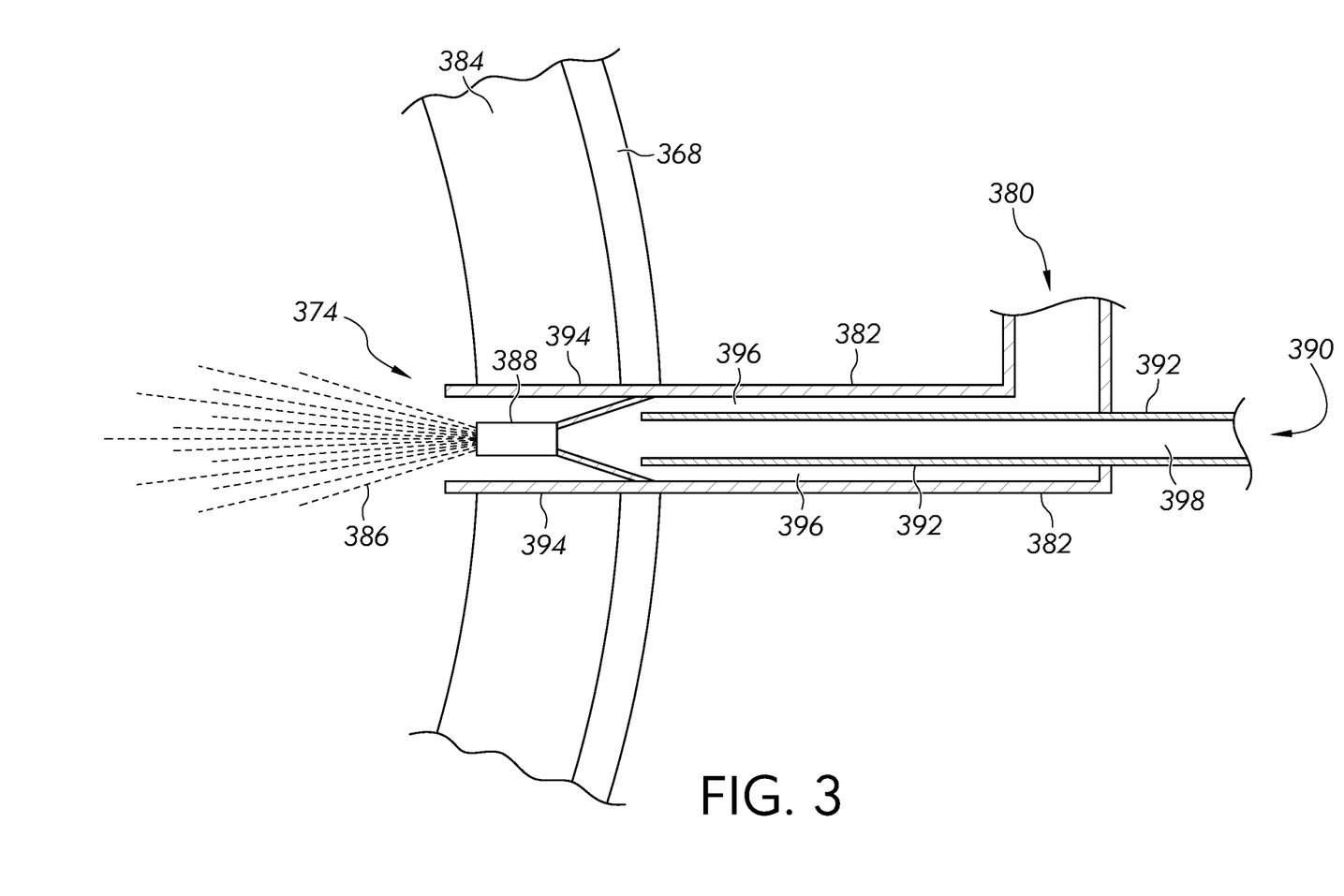
FIG. 3 schematically depicts an overhead cross-sectional view of a liquid injection port, according to one or more embodiments described herein.

Now referring to FIG. 3, an overhead cross-sectional view of an embodiment of a liquid injection port 374 is schematically depicted. According to one or more embodiments, the liquid injection port 374 may utilize a coaxial design wherein an axial flow path 398 is surrounded by a co-axial flow path 396. The axial flow path 398 may be defined by axial walls 392, which may be pipe-shaped. Co-axial flow path 396 may surround axial flow path 398 and be defined as the space between axial wall 392 and co-axial wall 382. Media may enter axial flow path 398 and co-axial flow path 396 through inlet 390 and inlet 380, respectively, and flow towards nozzle 388. The nozzle projects into the lower portion 368 of the regenerator (and through refractory material 384) and sprays liquid supplemental fuel 386. Walls 394 may project around the nozzle 388 to allow for the nozzle 388 to not be blocked by the refractory material 384.

In one embodiment, liquid supplemental fuel may be passed through the axial flow path 398 and a gas, such as nitrogen, may be passed through the co-axial flow path 396. The liquid fuel and gas may mix at or around the nozzle 388, and the liquid fuel may be atomized as it is sprayed from the nozzle 388.

For the purposes of describing and defining the present invention it is noted that the term "about" are utilized herein to represent the inherent degree of uncertainty that may be attributed to any quantitative comparison, value, measurement, or other representation. The term is also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the reactor system 102 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the reactor system 102 to which a pipe, conduit, tube, hose, transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for forming light olefins, the method comprising:
   introducing a feed stream into a reactor, the reactor comprising an upstream reactor section and a downstream reactor section, the upstream reactor section positioned below the downstream reactor section, and the upstream reactor section having an average cross-sectional area that is at least 150% of the average cross-sectional area of the downstream reactor section, wherein the upstream reactor section operates as a fast fluidized, turbulent, or bubbling bed upflow reactor;
   reacting the feed stream with a cracking catalyst in the reactor to from a product stream, wherein the feed stream comprises one or more of naphtha or butane, and the product stream comprises one or more of ethylene, propylene, or butene; and
   processing the cracking catalyst, the processing of the cracking catalyst comprising:
      passing the catalyst from the reactor to a combustor;
      burning a supplemental fuel source in the combustor to heat the catalyst; and
      passing the heated catalyst from the combustor to the reactor.

2. The method of claim 1, wherein the downstream reactor section operates as a dilute phase riser reactor.

3. The method of claim 1, wherein weight hour space velocity in the reactor is from 0.1 to 100 lb of feed stream per hour per lb of cracking catalyst in the reactor.

4. The method of claim 1, wherein the upstream reactor section has a superficial gas velocity of from 2 ft/s to 10 ft/s, and the downstream reactor section has a superficial gas velocity of from 30 ft/s to 70 ft/s.

5. The method of claim 1, wherein the ratio of catalyst to feed stream by weight is from 5 to 100.

6. The method of claim 1, wherein the cracking catalyst comprises one or more zeolites.

7. The method of claim 1, wherein the cracking catalyst comprises platinum.

8. The method of claim 1, wherein the supplemental fuel source comprises one or more of methane, natural gas, ethane, propane, hydrogen, fuel oil, kerosene, naphtha, or heavy cracking products.

9. The method of claim 1, wherein the supplemental fuel source comprises vapor supplemental fuel and liquid supplemental fuel, wherein the vapor supplemental fuel is injected into the combustor through a plurality of fuel gas distributors, and wherein the liquid supplemental fuel is injected into the combustor through one or more liquid injection ports.

10. A method for forming light olefins, the method comprising:
    introducing a feed stream into a reactor, the reactor comprising an upstream reactor section and a downstream reactor section, the upstream reactor section positioned below the downstream reactor section, and the upstream reactor section having an average cross-sectional area that is at least 150% of the average cross-sectional area of the downstream reactor section, wherein the upstream reactor section operates as a fast fluidized, turbulent, or bubbling bed upflow reactor and the downstream reactor section operates as a dilute phase riser reactor;
    reacting the feed stream with a cracking catalyst in the reactor to from a product stream wherein the feed stream comprises one or more of naphtha or butane, and the product stream comprises one or more of ethylene, propylene, or butene; and
    processing the cracking catalyst, the processing of the cracking catalyst comprising:
       passing the catalyst from the reactor to a combustor;
       burning a supplemental fuel source in the combustor to heat the catalyst; and
       passing the heated catalyst from the combustor to the reactor.

11. The method of claim 10, wherein the upstream reactor section has a superficial gas velocity of from 2 ft/s to 10 ft/s, and the downstream reactor section has a superficial gas velocity of from 30 ft/s to 70 ft/s.

12. The method of claim 10, wherein the ratio of catalyst to feed stream by weight is from 5 to 100.

13. The method of claim 10, wherein the catalyst flux in the upstream reactor section is from 1 lb/ft$^2$-s to 20 lb/ft$^2$-s.

14. The method of claim 10, wherein the supplemental fuel source comprises one or more of methane, natural gas, ethane, propane, hydrogen, fuel oil, kerosene, naphtha, or heavy cracking products.

15. A method for forming light olefins, the method comprising:
    introducing a feed stream into a reactor, the reactor comprising an upstream reactor section and a downstream reactor section, the upstream reactor section positioned below the downstream reactor section, and the upstream reactor section having an average cross-sectional area that is at least 150% of the average cross-sectional area of the downstream reactor section, wherein the upstream reactor section operates as a fast fluidized, turbulent, or bubbling bed upflow reactor, and wherein the feed stream comprises one or more of naphtha or butane;

reacting the feed stream with a cracking catalyst in the reactor to form a product stream, wherein the product stream comprises one or more of ethylene, propylene, or butene; and processing the cracking catalyst, the processing of the cracking catalyst comprising:
  passing the catalyst from the reactor to a combustor;
  burning a supplemental fuel source in the combustor to heat the catalyst; and
  passing the heated catalyst from the combustor to the reactor.

16. The method of claim 15, wherein the supplemental fuel source comprises one or more of methane, natural gas, ethane, propane, hydrogen, fuel oil, kerosene, naphtha, or heavy cracking products.

\* \* \* \* \*